US012723983B2

(12) United States Patent
Zhang et al.

(10) Patent No.: US 12,723,983 B2
(45) Date of Patent: Sep. 1, 2026

(54) APPARATUS AND METHOD FOR NON-CONTACT DETECTION OF HYDROCARBON AND OTHER FLUORESCENCE MATERIALS ON A SURFACE

(71) Applicant: CLEARVIEW SENSING, INC., Richmond, TX (US)

(72) Inventors: Jianfeng Zhang, Sugar Land, TX (US); Jurgen Zach, Lafayette, IN (US)

(*) Notice: Subject to any disclaimer, the term of this patent is extended or adjusted under 35 U.S.C. 154(b) by 198 days.

(21) Appl. No.: 18/699,603

(22) PCT Filed: Jan. 2, 2023

(86) PCT No.: PCT/US2023/060003
§ 371 (c)(1),
(2) Date: Apr. 9, 2024

(87) PCT Pub. No.: WO2023/081937
PCT Pub. Date: May 11, 2023

(65) Prior Publication Data
US 2024/0418651 A1 Dec. 19, 2024

Related U.S. Application Data

(60) Provisional application No. 63/275,993, filed on Nov. 5, 2021.

(51) Int. Cl.

| | |
|---|---|
| ***G01N 21/64*** | (2006.01) |
| ***G01N 21/94*** | (2006.01) |
| ***G01N 33/28*** | (2006.01) |

(52) U.S. Cl.
CPC ......... *G01N 21/6456* (2013.01); *G01N 21/94* (2013.01); *G01N 33/28* (2013.01); *G01N 2021/6463* (2013.01); *G01N 2021/945* (2013.01); *G01N 2201/129* (2013.01)

(58) Field of Classification Search
CPC .... G01N 21/6456; G01N 21/94; G01N 33/28; G01N 2021/6463; G01N 2021/945; G01N 2201/129; G01N 21/278; G01N 2021/6421; G01N 2201/1296; G01N 2201/0212; G01M 3/207; G01M 3/22
See application file for complete search history.

(56) References Cited

U.S. PATENT DOCUMENTS

2007/0210262 A1* 9/2007 Pearlman .......... G01N 33/1833 356/70

* cited by examiner

*Primary Examiner* — Courtney D Thomas
(74) *Attorney, Agent, or Firm* — Ingenium Patents LLC; Peter R Kramer

(57) ABSTRACT

An apparatus and method for detecting certain materials on a surface using the fluorescence principle. The invention is suitable for materials that emit fluorescence when excited by high energy (short wavelength) visible light or ultraviolet light. The apparatus irradiates a surface to be monitored with excitation light. The light that returns from the surface is analyzed. Fluorescence in the returned light signals the presence of the material to be detected. The invention uses light-emitting diodes, lasers, or other light sources to generate the excitation light, light-sensing integrated circuits or imaging sensors for measuring the fluorescence signals from materials on the monitored surface, light sensors for evaluating the excitation light, and operates with on and off cycles of the excitation light to obtain the signal.

12 Claims, 11 Drawing Sheets

(a)

(b)

(a)

(b)

Figure 1:
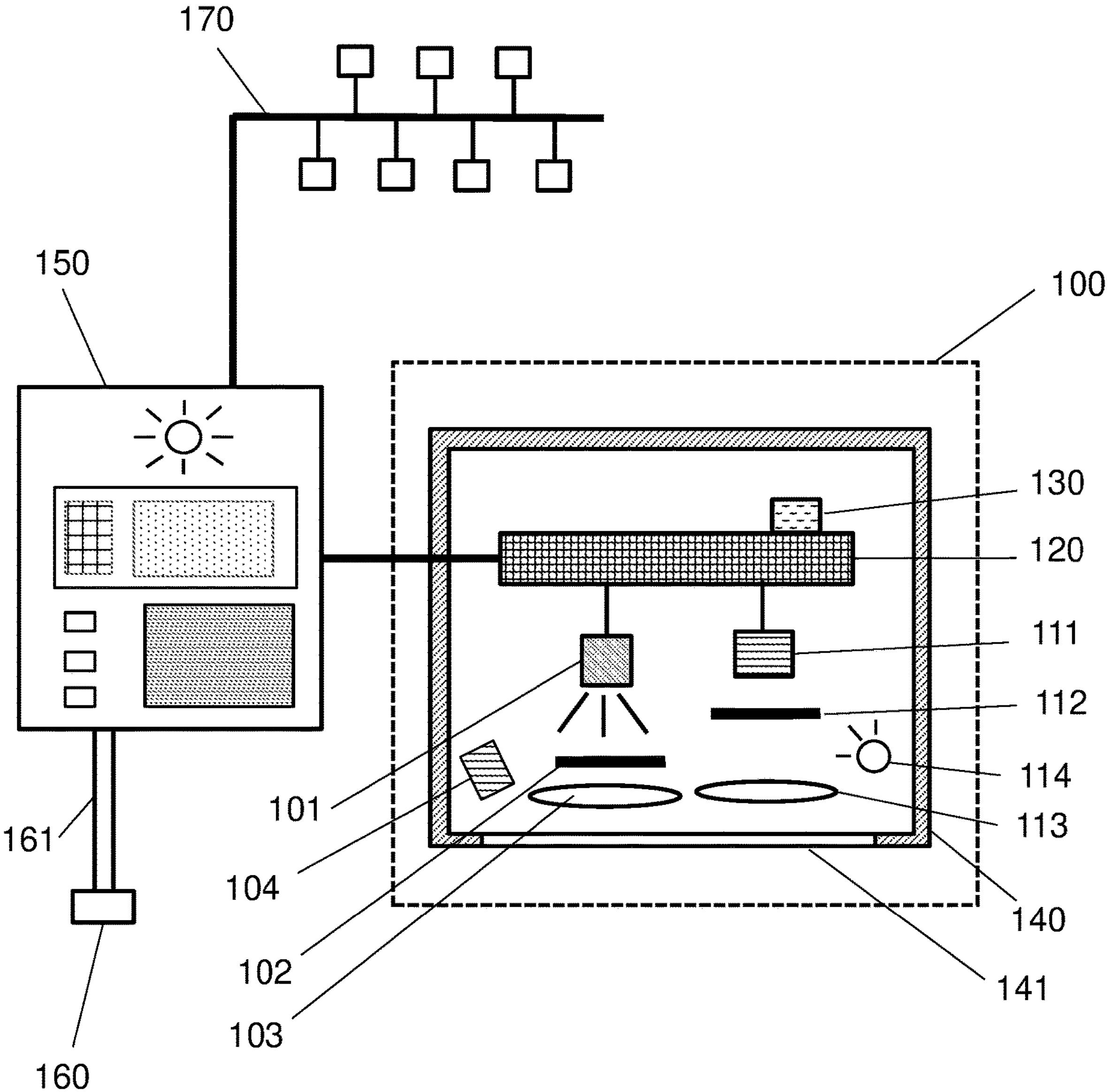

APPARATUS AND METHOD FOR NON-CONTACT DETECTION OF HYDROCARBON AND OTHER FLUORESCENCE MATERIALS ON A SURFACE

BACKGROUND OF THE INVENTION

Field of the Invention

The field of the invention is an apparatus and method for detecting the presence of hydrocarbon or other fluorescent materials on solid or liquid surfaces. Examples of the application include the detection of hydrocarbon fuel leakage in generator rooms, detection of heating oil leakage, detection of leakage of aviation fuels in aircraft hangars, airports, and land-based and sea-borne runways and landing pads, detection of fuel accumulation in storm water sumps, detection of leakage from industrial plants processing hydrocarbons including but not limited to refineries, detection of leakage from hydrocarbon storage such as in tank farms or fueling stations, detection of free oil in the discharge of produced water into sea from offshore oil and gas production facilities, detection of free oil in water tanks or ponds, detection of hydrocarbon-based, other fluorescent lubricants, or lubricants with fluorescent additives leaking from generators, machines, motors, or other equipment, detection of the leakage of organic fluids for electrical insulation such as transformer oil, and detection of environmental pollution in rivers and lakes due to hydrocarbons or other fluorescent chemicals.

Description of Related Art

Various apparatus and methods for detecting hydrocarbon fuel and crude oil on floors or water surfaces have been described in patents or applications for patents. These are represented by the following:

1. Detection by contact: U.S. Pat. No. 3,719,936 (1973), U.S. Pat. No. 3,733,594 (1973), U.S. Pat. No. 4,029,889 (1977), U.S. Pat. No. 4,119,860 (1977), U.S. Pat. No. 4,131,773 (1978), U.S. Pat. No. 4,206,632 (1980), CA 1106027A (1981), U.S. Pat. No. 4,434,650 (1984), U.S. Pat. No. 4,487,507 (1984), U.S. Pat. No. 4,563,674 (1986), U.S. Pat. No. 4,870,292 (1988), U.S. Pat. No. 5,005,005 (1989), U.S. Pat. No. 5,159,276 (1992), WO 92/07249 (1992), U.S. Pat. No. 5,244,813 (1992), U.S. Pat. No. 5,291,032 (1993), U.S. Pat. No. 5,452,076 (1993), U.S. Pat. No. 5,422,495 (1993), U.S. Pat. No. 5,507,326 (1994), U.S. Pat. No. 5,481,904 (1996), U.S. Pat. No. 5,532,679 (1996), U.S. Pat. No. 5,946,084 (1998), U.S. Pat. No. 6,278,106 B1 (1998), U.S. Pat. No. 5,982,959 (1998), EP 0722614 B1 (2000), Chinese Patent 100437093C (2000), Chinese U.S. Pat. No. 2,898,800Y (2006), Chinese Patent 2898815Y (2006), JP2011185926A (2010). Japanese Application JPH1194688A (1997), US Application 2008/0144033 A1 (2008), US Application 2009/0051554-A1 (2009), US Application 2015/0362355 (2015), US Application 2014/0125496 (2014),
2. Non-contact detection: U.S. Pat. No. 4,897,551 (1990), WO 92/07249 (1992), Japanese Patent JP3869070B2 (1997), U.S. Pat. No. 4,897,551 (1988), U.S. Pat. No. 5,974,860 (1999), U.S. Pat. No. 6,717,658 B1 (2000), U.S. Pat. No. 7,417,228 B2 (2008), WO 2009/023552 A3 (2009), U.S. Pat. No. 7,688,428 B2 (2010), EP 1639387 B1 (2010), WO 2014/075724 A1 (2014), German Application DE2657851A1 (1978), Japanese Application JP2001153800A (1999), Japanese Application JP2002139423A (2000), Japanese Application JP2003149146A (2001), US Application 2003/0072004 A1 (2003), US Application 2005/0122225 A1 (2005), International Application WO 2012/021753 A3 (2012), US Application 2016/0061665 A1 (2016).

Devices made with the related art have been used with various degree of success. However, at least one or more among the following shortcomings have been encountered by the related art, depending on the particular art, Requiring time-consuming and manual reset of the sensing element after detection, Creating waste fluid during calibration, verification and/or reset, Giving rise to responses too slow for fire prevention needs, Being unable to detect very thin film such as oil sheen, Being limited to monitoring a localized spot, For devices monitoring an area, requiring the monitored area to be mostly covered by hydrocarbon, and not being able to detect the presence of hydrocarbons located in a small sub-area within the monitored area, Requiring deep Ultraviolet (UV) light generated by lamps, which need to be changed frequently for continuous monitoring service, and that may be harmful to humans present, Being vulnerable to influences by certain environmental conditions such as the amount of certain spectral light components in artificial lighting, Not being able to distinguish between water and hydrocarbons, Exceeding size constraints for some facilities, Being too costly for some applications, for example hazardous locations such as generator rooms or pump rooms.

Therefore, there exists the need for a high sensitivity, non-contact sensor that is suitable for both safe locations and hazardous locations, that offers a low cost of ownership and is easy to reset and calibrate, to detect the presence of hydrocarbon fuel, crude oil, lubrication fluids and other fluids on surfaces.

BRIEF SUMMARY OF THE INVENTION

The present invention is an apparatus and method which detects the presence of certain materials on a surface using the fluorescence principle. The invention is suitable for materials that emit fluorescence when excited by high energy (short wavelength) visible light or ultraviolet light. When the excitation light meets the material, a portion of the light is absorbed by the molecules of the material. The molecules change to an excited state of higher energy, then relaxes to a state of lower energy than the excited state through emission of photons, which is the fluorescence. Fluorescence usually has longer wavelength than the excitation light. A portion of the excitation light is reflected back by the material, and the reflected light has the same wavelength as the excitation light. The apparatus irradiates a surface to be monitored with excitation light, for example visible or ultraviolet light. The light that returns from the surface is analyzed. Fluorescence in the returned light signals the presence of the material to be detected. The invention uses light-emitting diodes, lasers, or other light sources to generate the excitation light, light-sensing integrated circuits or imaging sensors for measuring the fluorescence signals from materials on the monitored surface, light sensors for evaluating the excitation light, and operates with on and off cycles of the excitation light to obtain the signal. The fluorescence sensors may be point sensors, imaging sensors such as those used in digital cameras, arrays of sensors such as found in vision systems, or spectral imaging sensors. The fluorescence sensors generate signal magnitude readings on one single color (the response to signal peaks at a certain light wavelength and reduces quickly when the wavelength deviates from this value), multiple colors, spectra of signal strength versus wavelength, or the overall strength over a broadband range of wavelengths. During each cycle, the signal magnitude readings can be a single value for the whole monitored area, or a 2-dimensional matrix describing the signal from different locations of the monitored area. Digital or analog signals representing fluorescence are subjected to time-series data analysis using sophisticated algorithms to eliminate false positives to enable a high sensitivity, low maintenance, low-cost, and compact non-contact sensing device for detecting hydrocarbons and other fluorescent materials on surfaces. The algorithms include state-of-the-art image recognition based on neural network-, deep-learning-, and other machine learning methods.

BRIEF DESCRIPTION OF THE SEVERAL VIEWS OF THE DRAWING(S)

FIG. 1 Components of the apparatus in one embodiment.

Figure 2:
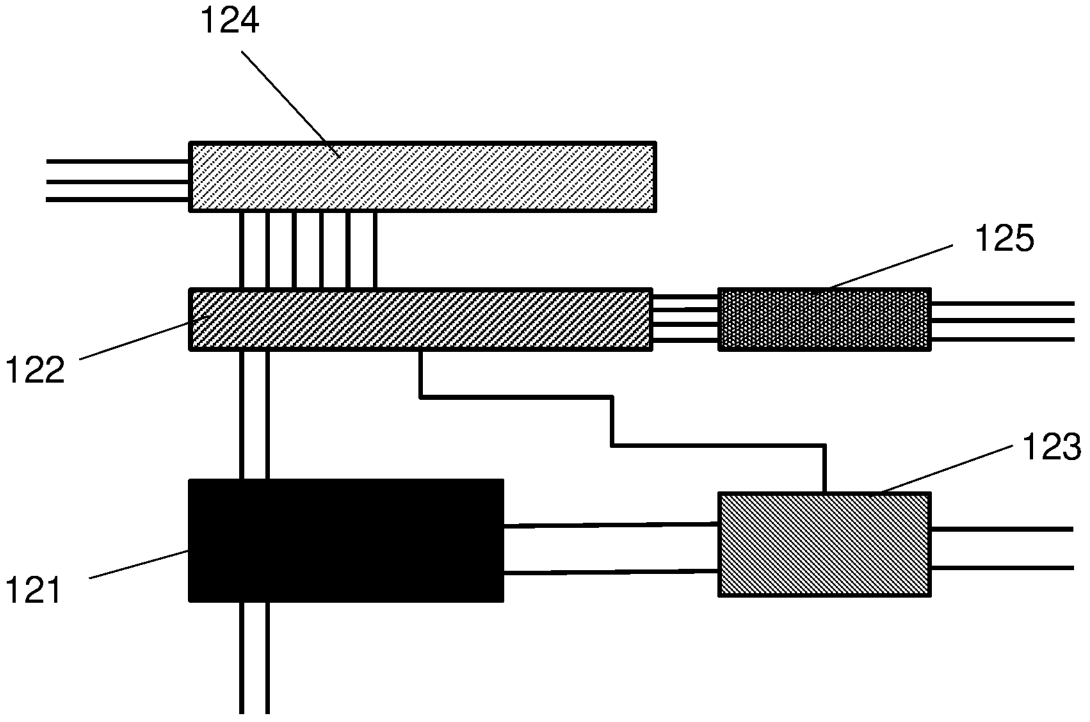

FIG. 2 Details of electronic circuits and digital processing devices (Component 120 in FIG. 1)

Figure 3:
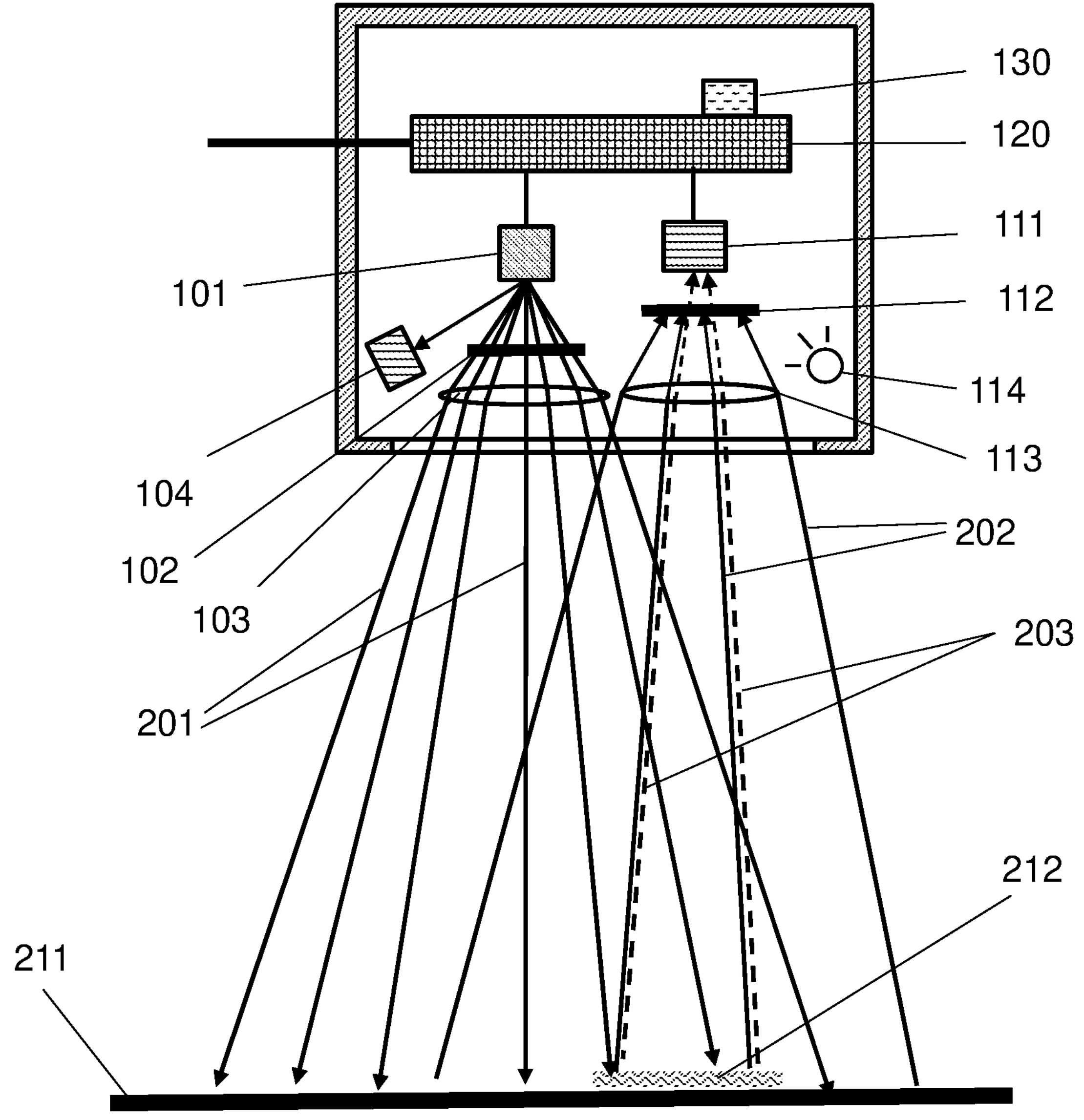

FIG. 3 Schematic view of a typical application of the invention, where the apparatus is installed directly above the surface to be monitored.

Figure 4:
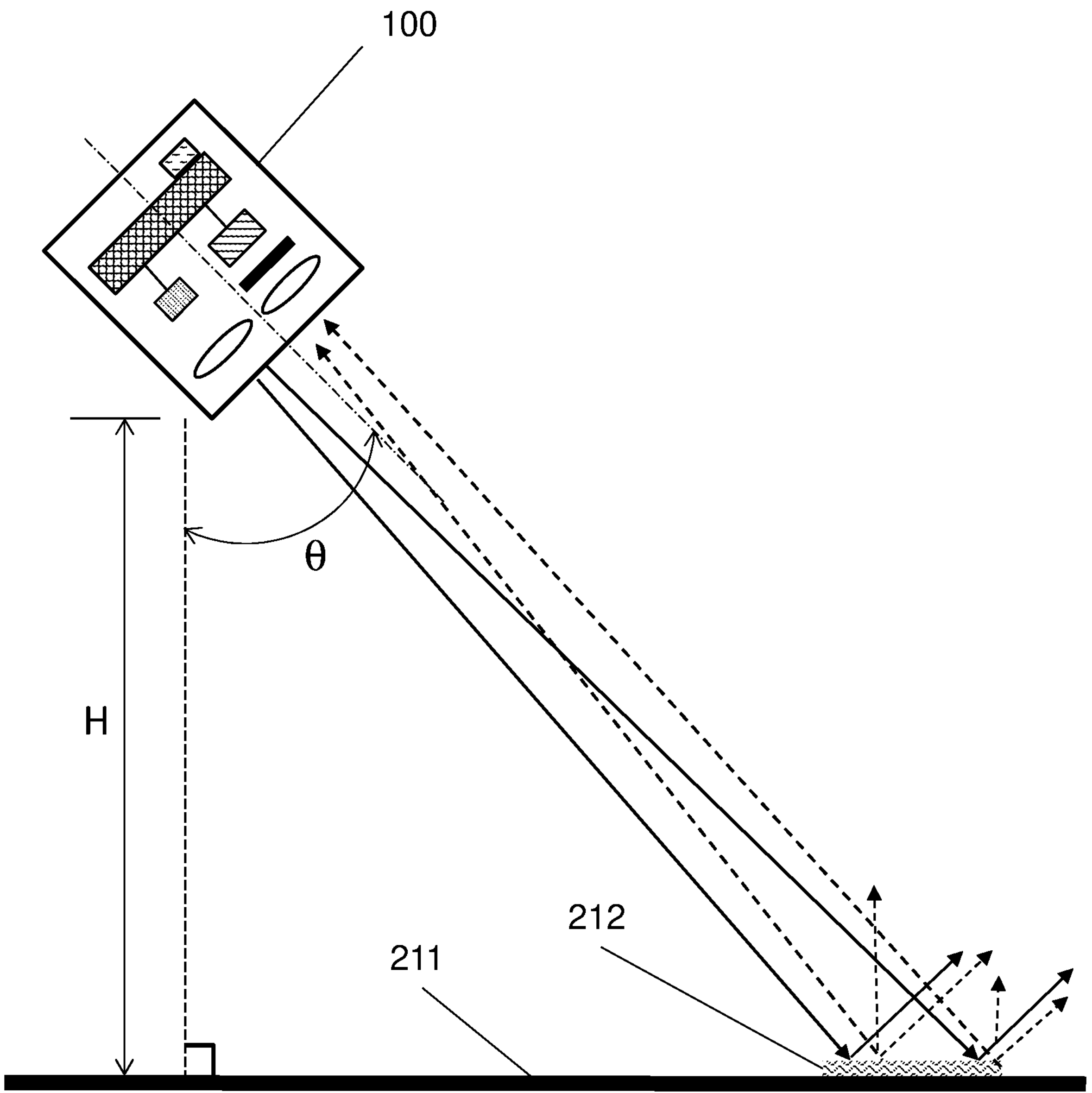

FIG. 4 Schematic view of a typical application of the invention, where the apparatus is installed at an angle from the surface, or operated in a scanning manner.

Figure 5:
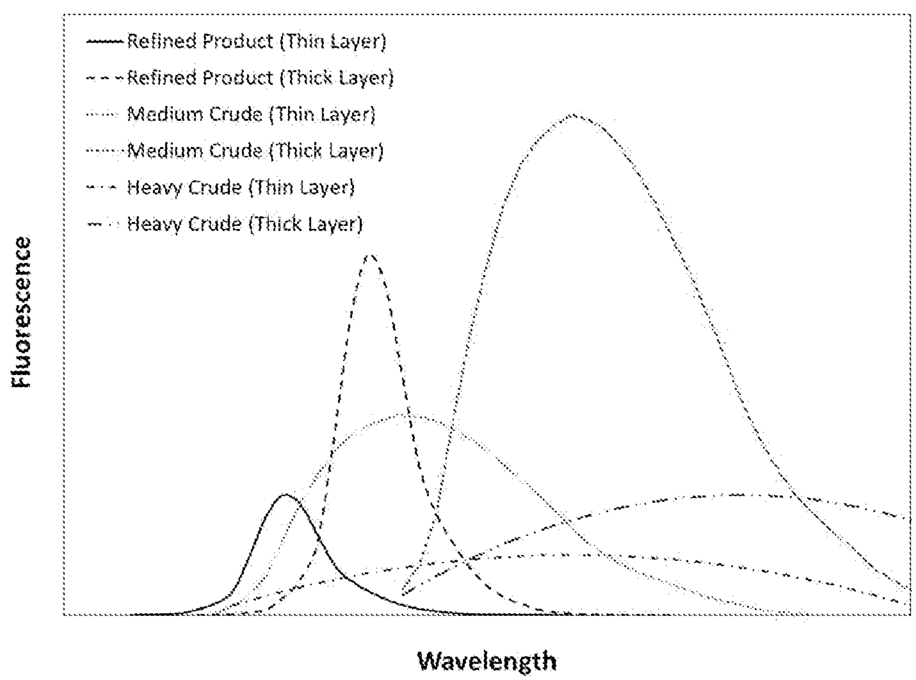
Figure 6:
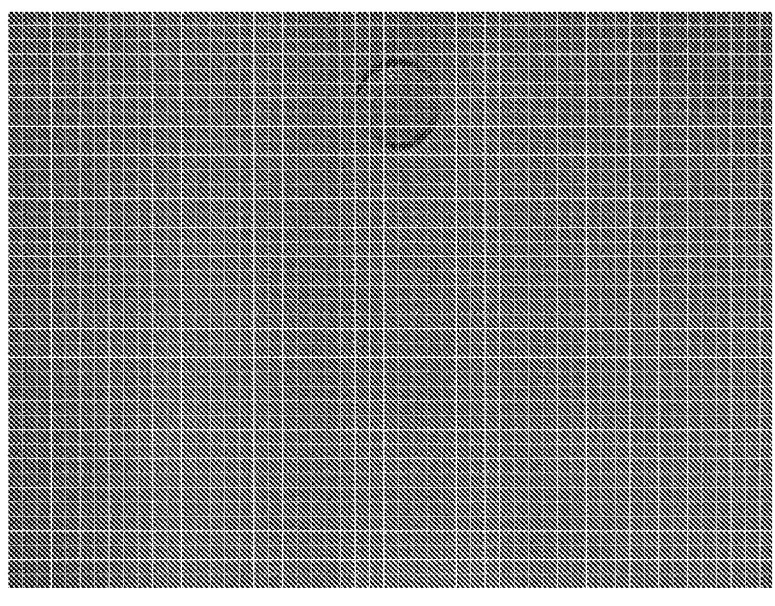
Figure 6:
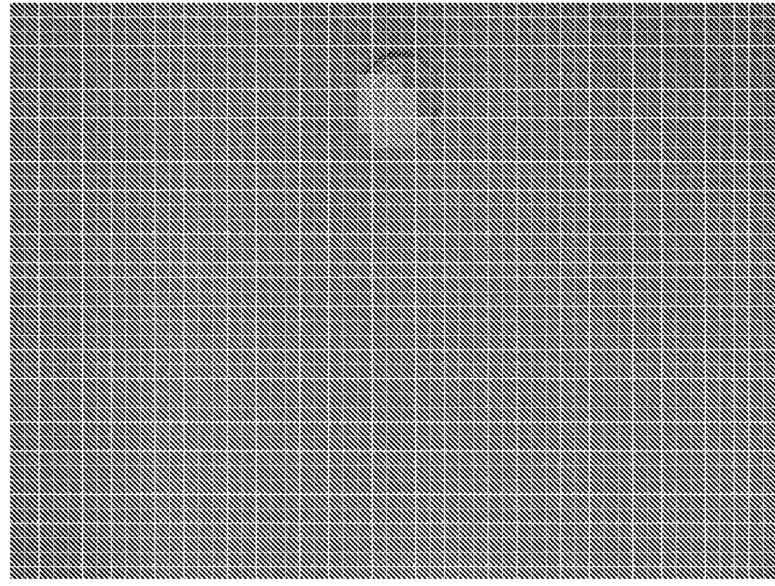

FIG. 5 Illustrative fluorescence spectra and red-shift phenomena for different hydrocarbons FIG. 6 Example image of the monitored area, division of the monitored area into blocks, and a map of hydrocarbons detected.

Figure 7:
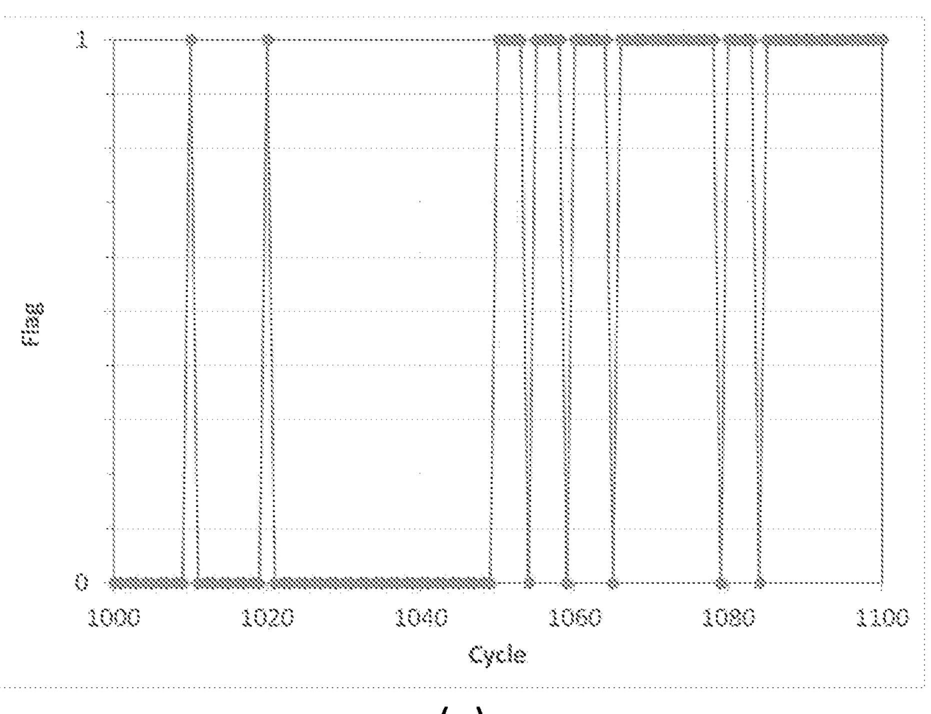
Figure 7:
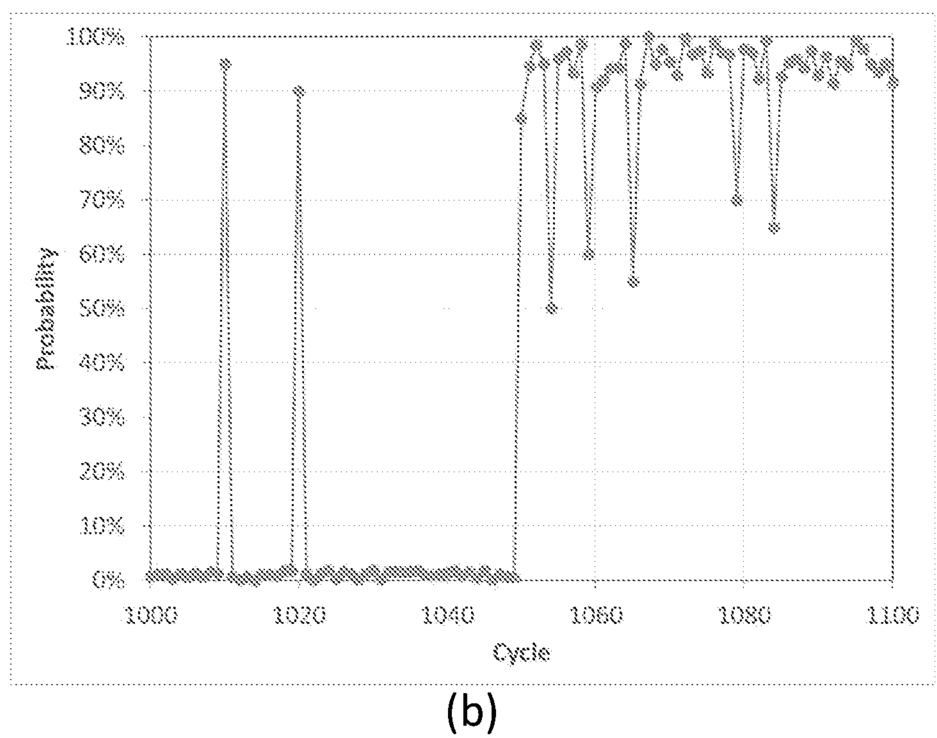
Figure 8:
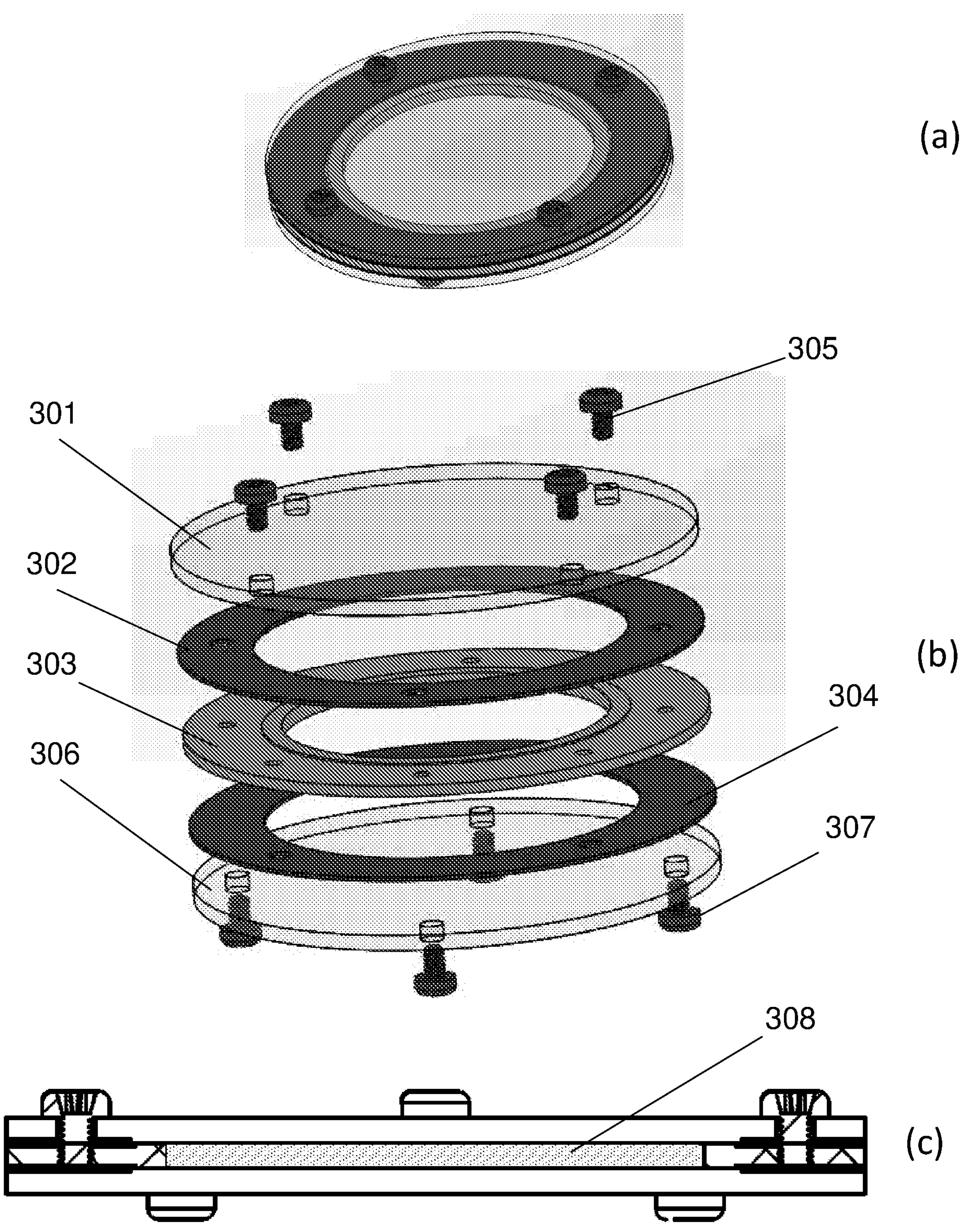
Figure 9:
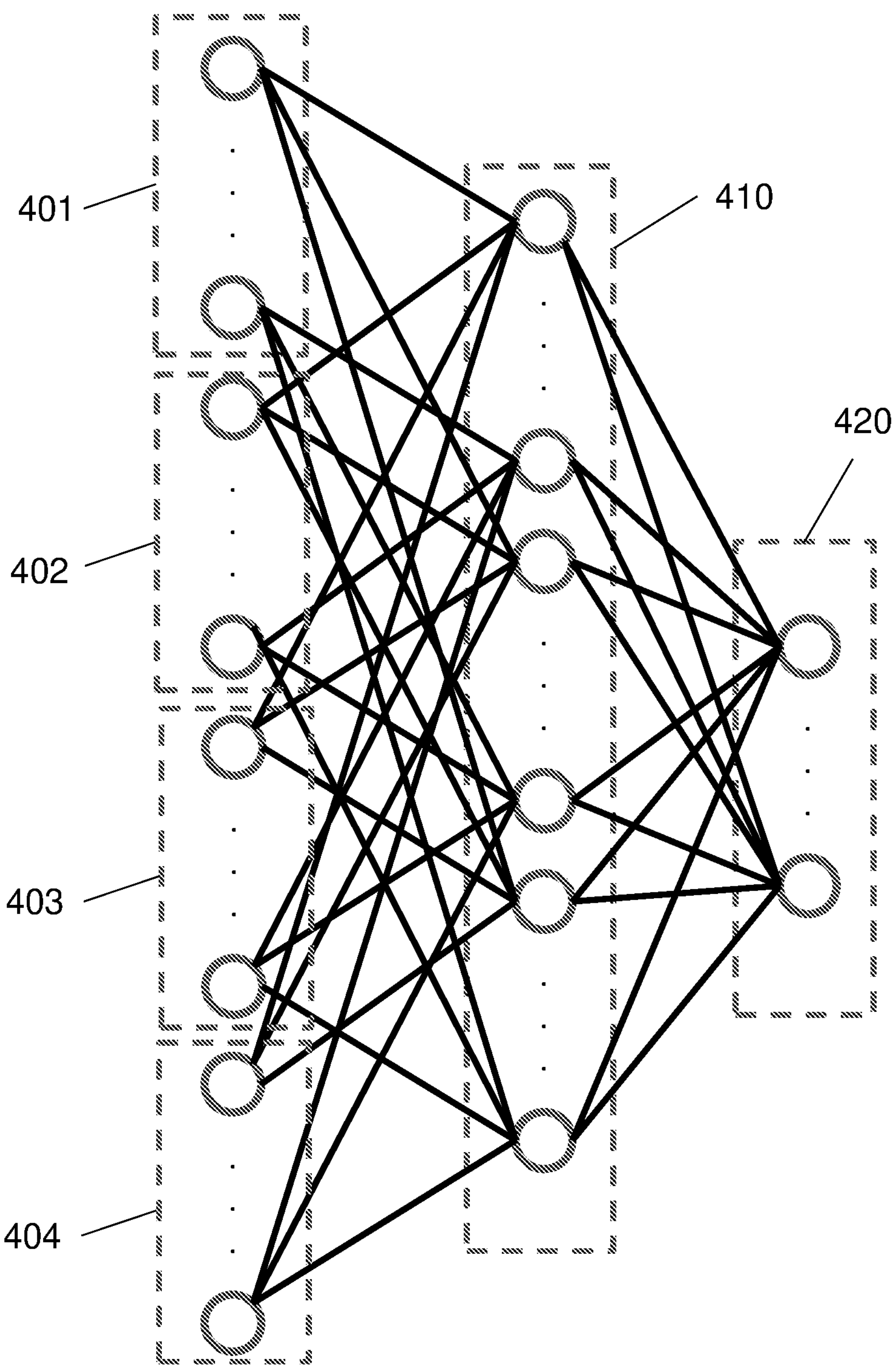

FIG. 7 Example time series for the flag and probability of hydrocarbon presence FIG. 8 Example of calibration and verification sample and container FIG. 9. Example Implementation of Artificial Neutral Network FIG. 10 Embodiment with light transmitter subsystem and light receiver subsystem in separate enclosures FIG. 11 Embodiment with one light transmitter subsystem and multiple light receiver subsystems

DETAILED DESCRIPTION OF THE INVENTION

It is known that certain materials emit fluorescent light, or fluorescence, under excitation by light of a suitable wavelength, such as from the ultraviolet or visible spectrum. If the material is transparent and spread over a surface area, the strength of the fluorescence generally increases with the thickness of the material until a plateau is reached. If the material is non-transparent, the strength of fluorescence generally increases with the surface area of the material. Furthermore, the spectra of fluorescence may differ significantly between materials, and the spectra for transparent materials may change with the thickness. These characteristics can be used to determine whether the amount of the material is over a certain threshold and can be used to identify the material present and estimate its amount.

The invention is scalable through the amount of illumination provided, from small areas with cross sections of just millimeters or centimeters to very large areas with cross sections of tens or hundreds of meters.

As an example, fluorescence by artificial light excitation can be used to determine whether there is any hydrocarbon fuel having leaked onto the floor of a generator room that is normally free of the fuel, where the area to be observed is typically a few meters wide. As another example, fluorescence can be used to determine whether the sea surface around an offshore oil and gas facility discharging water overboard has any free oil, where the observed area would be tens or hundreds of meters wide. As a further example, a fluorescence-based method can be used to detect potentially hazardous leaks of aviation gas or jet fuel leaking from fuel storage or during refueling operations of aircraft, where the sensor can be stationary or mounted on aircraft or ground vehicles. Yet another example application are fuel tanks and engines of watercraft to prevent fire hazard and environmental contamination of waterways. Said watercraft may include vessels transporting hydrocarbons (such as supertankers), as well as their hydrocarbon stores. As an additional example, fluorescence can be used to detect leaking hydrocarbons or other fluorescent chemicals which are produced or processed in industrial operations such as oil refineries, where they will be detectable on floors or surfaces which are normally free of hydrocarbons. Further examples include fluorescence to be used to detect fluorescent lubricants and cooling liquids, typically hydrocarbon-based, from machinery, generators, engines, or transformers.

Another example are miniaturized form factors, such as for leak detection in commercial fueling stations. These may be compact sensor packages on printed circuit boards in small enclosures. Other embodiments may include even further miniaturization as lab-on-chip- or optoelectronic application-specific electronic circuit (ASICs) versions, in which much or all of the components are included in a single semiconductor package. Such miniaturized embodiments can be deployed as general-purpose hydrocarbon sensors for integration into a wide range of applications including engines of ground vehicles, watercraft, or aircraft, heaters burning liquid hydrocarbons, and low-cost distributed sensors for environmental monitoring.

In all applications mentioned, whether miniaturized or not, it should be mentioned that the fluorescence of liquids can often be safely enhanced through the use of fluorescent additives, thus increasing the sensitivity of the present invention.

Previous implementations of this detection principle have used xenon lamps or UV LED for excitation light and photodiodes for detection. The inventors of the present technology discovered that visible light LEDs or laser diodes, with the center of the emission wavelengths longer than nm, can be used to effectively excite the material for fluorescence. Using visible light also improves light safety. The present inventors also discovered that light sensors such as Complementary Metal-Oxide-Semiconductor (CMOS) or Charge-Coupled Device (CCD) can be used to form highly sensitivity apparatuses to measure the magnitude of the fluorescent light, from which the presence of the fluorescence materials can be determined.

The inventors further discovered that both the overall magnitude of the signal from the monitored area, measured by either a single light sensor or integrating from the data of an imaging sensor, and -dimensional matrix of signals detailing the fluorescence from individual locations of the monitored area are useful for detecting and quantifying the materials detected.

The inventors further discovered that the fluorescence spectrum from the monitored area can be used to identify the type of material present and to estimate its thickness, and that the fluorescence spectra from individual locations within the monitored area can be used for the same purpose at each of the locations.

The inventors further discovered that it is advantageous, in certain applications, to form an image of the monitored surface, with the image containing the characteristics of the fluorescence emitted from, or light reflected from, the surface, and to divide the image into subgroups corresponding to surface locations for further analysis. The image can be monochrome, color or multi-spectral. The subgroups can be individually analyzed, then combined to increase detection accuracy and to detect small-volume leakage.

The descriptions herein use hydrocarbons as the materials to be monitored, since hydrocarbons are the type of materials in many applications. However, the system and method of this invention are also applicable for other organic and inorganic materials which can generate fluorescence, for example, chlorophyll, quinine, humic acids, fulvic acids, solutions of certain manganese salt solutions, solutions of certain sulfate salt solutions, and sulfuric acid. The same systems and methods can also be used to detect the appearance or accumulation of solid materials and vapor that emit fluorescence under the excitation of light. If a fluorescent additive can be successfully mixed in with the fluid which is targeted for leak detection without interfering with its intended function, create hazards, or create regulatory conflicts, the same systems and methods can be used for any fluid, fluorescent or not, which lends itself to the admixture of a fluorescent additives by mixing of liquids or dissolving of solids.

One preferred configuration of the apparatus and method is comprised of a sensor and a controller, and is illustrated in FIG. 1, where:

100 is the sensor of the apparatus, which will be installed with a line of sight relative to the surface to be monitored. It is comprised of components 101 through 141.

101 is an emitter of ultra-violet or visible light with wavelengths from a narrow band selected from within the range from ultraviolet to visible light. In many embodiments, a particularly preferred emitter is one single-color light emitting diode (LED) with a wavelength between 400 and 550 nm, or a group of LEDs with wavelengths between 400 to 550 nm. The LEDs in the group can have the same wavelength, or multiple wavelengths. In much larger or much smaller embodiments, the light sources are appropriately scaled up or down.

Other wavelengths in the range from 100 nm-600 nm can also be used. For example, wavelengths centered at values smaller than 250 nm can be used for certain hydrocarbon products which only emit fluorescence with excitation wavelength in that range. As another example, wavelengths centered around 550 nm can be used if other ultra-violet or visible light wavelengths are not desirable for the application, and the hydrocarbons have either inherent components or additives that emit fluorescence under such excitation light wavelengths.

In other embodiments, a laser diode or group of laser diodes of the same wavelength range can be used as the light source. Using laser diodes is particularly preferable when the monitored surface is spot-wise scanned or systematically "swept" (in patterns of lines and columns) to reach full coverage.

102 is an optional short-pass or band-pass optical filter that blocks light components with wavelengths longer than a threshold value or blocks light components with wavelengths outside a certain wavelength band. 102 is needed if light sensing element 111 does not distinguish the portion of light with the fluorescence wavelength from the portion of light with the excitation wavelength, such as an ambient light sensor. 102 is not required if light sensing element 111 can distinguish the portion of light with the fluorescence wavelength from the portion of light with the excitation wavelength, such as a spectral sensor or a color imaging sensor.

103 represents a lens or an assembly of lenses, with fixed or adjustable focal length, to turn the light from 101 into a light beam with a desired beam angle to cover the area of interest on the surface to be monitored.

104 is a light sensing element for assessing the strength of light emitted by 101. The readings from the sensor are used to adjust the drive current for 101, normalize the fluorescence readings by 111, or both.

111 is the primary light sensing element of the sensor. It is used to sense the light returned from the surface to be monitored. The light returned contains fluorescence, if any, emitted from the materials on the surface and reflected light from the surface. A preferred type of sensing element is a light-to-digital single Complementary Metal-Oxide-Semiconductor (CMOS) semiconductor integrated circuit. Another preferred type of the sensing element is a semiconductor sensing array, which is an imaging sensor with an array of pixels such as a CMOS, a Charge-Coupled Device (CCD), multispectral sensor, or another imaging sensor capable of generating two-dimensional representations of the scene containing said surface by conducting wavelength-sensitive measurements in each pixel. The semiconductor sensing array can be adapted for the acquisition of a color image (such as red, green, and blue pixels), or for a monochrome image. The multispectral sensors can be adapted either for a single set of spectral measurements, or for a spectral image. The multispectral sensor is capable of producing readings on the strength of light in a number of wavelength bands for all light received, or such data corresponding to locations on the monitored surface.

112 is a long-pass or band-pass optical filter. It transmits light with wavelengths longer than a first threshold value and blocks light with shorter wavelengths. When 112 is a band pass filter, it also blocks light with wavelengths longer than a second threshold, which can be used for the purpose of improving signal to noise ratio. The first threshold wavelength is a certain amount (typically 50 to 100 nm) longer than the wavelength of light from 101, and also longer than the cutoff wavelength of the short-pass filter 102, if the short-pass filter 102 is used. The second threshold is selected through the selection of a band pass filter to match the fluorescence signatures of the hydrocarbon or hydrocarbons to be detected.

113 is a lens or assembly of lenses, with fixed or adjustable focal length, to direct the light from the monitored surface to sensing element 111. Lens 113 is optional if sensing element 111 is a single CMOS integrated circuit or other type for which the signal generated is not dependent on the location on the surface monitored. Lens or lens assembly 113 is required if sensing element 111 is an imaging sensor, including monochrome imaging sensor, color imaging sensor and spectral imaging sensor, and generates a set of signals that are dependent on the location on the surface monitored.

114 is an optional auxiliary visible light source to assist the operation of sensing element 111.

120 is an electrical circuitry and digital processing unit. It includes a combination of electronic circuits and digital processing devices. The details of the unit are illustrated in FIG. 2. It provides power to light emitters 101 and 114, analyzes the data collected from sensing elements 104 and 111, and controls all components within sensor 100. It also interfaces with controller 150, and wireless communication component 130, if such is present.

130 is an optional component to connect with external networking devices using wireless communication protocols such as Wi-Fi, LoRa (Long Range) wide-area network protocol, Bluetooth, or any other radio frequency-based wireless network technology.

140 is an enclosure for components 101 through 130.

141 is an optical aperture for the emitted light, the reflected light, and fluorescence emissions from the monitored surface to pass through.

150 is a controller that communicates with, and may provide power to, sensor 100, unless sensor 100 has its own power supply. It also includes local alarm indicators, user interfaces and communications systems with other network devices such as building-, site- or facility control systems or cloud-based control systems through local networks, wide-area networks, intranets, or the World Wide Web. The local alarm indicators include visual- or audio-indicators such as warning lights, warning displays, warning sound actuators, or sirens.

Controller 150 may also include relays and logical outputs. One controller 150 can be connected with one sensor 100 or multiple sensors. Controller 150 can be installed close to sensor 100, installed at some distances away, or combined with sensor 100 in a single housing.

Sensor 100 can be used together with controller 150 or operated directly by the control system via common communication protocols such as Modbus or BACnet.

Many variations of the hardware configurations of sensor 100 can be used to suit specific requirements of a monitoring application. As one example, a scanning assembly can be added inside sensor 100, on which 101, 102, 103, 104, 111, 112, 113, 114 are mounted. The optical configuration would then be such that a small spot of the surface is lighted. The scanning assembly systematically changes the direction of the excitation light beam to cover the full monitored area in one round of scanning. The signal received is tagged with the beam direction at the time of the signal and correspondingly the location on the monitored surface.

FIG. 2 illustrates the details of electrical circuitry and digital processing unit 120 shown in FIG. 1. The components of the electronics and digital processing are comprised of

- A power converter 121, which is connected to an external power source and converts the power supplied to the form required by other components of the sensor, for example, converting from alternating current to direct current of one or more suitable voltages, or convert from one voltage level of direct current to one or more different voltage levels needed. It may be connected to a rechargeable or non-rechargeable backup battery in case of a power outage.
- A processing unit 122 for data processing and control functions. A Processing Unit is defined as a microcontroller, central processing unit, or any other digital computer with memory for a program and data, with the memory either included or attached, either as volatile or non-volatile memory or a combination of both, wherein the processing unit is designed to store digital data and execute computing programs. The processing unit can store program data, acquired data, processed data, and event logs. The processing unit also has logical output capabilities. The processing unit runs a software or firmware installed on it to operate the emitter driver circuit to light up the surface to be monitored, analyze the light data measured by the sensing element 111, interface with the communication circuit to produce data for the controller 150 or received data from it, drive the wireless communication component 130, and produce the output needed for activating the analog indication signals.
- In some embodiments that have higher computation requirements or require certain special processing capabilities, a second processing unit may be used. In this case, the computation-, control-, and communications tasks are divided between the two processing units. The second processing unit is not shown in FIG. 2.
- An emitter driver circuit 123 to power light emitter 101. The emitter driver circuit provides constant drive current to the light source and is powered by the power supply 121. The emitter driver circuit outputs the required electrical current for the emitter to light up at constant or varying light intensities or reduces the output current to zero for turning off the emitter, based on the relevant control output from the microcontroller 122.
- A communications circuit 124 that communicates with controller 150 using wired or wireless communication. Examples for wired or wireless communication devices include, but are not limited to: a wired or wireless modem communicating with a local network, wide-area network, the world wide web, or any other network; a radio frequency node such as a Bluetooth radio, LoRa wireless radio, or any other wireless network; a wired communication node such as Modbus, BACNet, or any other open or customized wired protocol; a cellular telephony node; a satellite communications node.
- A circuit 125 to produce analog or digital, local or remote indications when a positive determination has been made, and indications on the operational status of the device,
- The un-numbered lines represent wiring, pins, solders, printed circuits, or other suitable electrical connections between the components, or between the components and other components inside sensor 100 or external devices. The numbers of wires in the drawings do not necessarily represent the number of wires in the specific embodiment.

Emitter driver circuit 123 and parts of power supply circuit 121 and processing unit 122 comprise the power controller that modulates the light intensity from the transmitter following a predetermined function of time, such as switching full power on and off at predetermined regular or irregular intervals. In most embodiments, the processing unit 122 synchronizes the modulation of power to the transmitter and the activation and light accumulation at light sensing element 104. In some embodiments, the two activities are not synchronized and the processing unit 122 deduces the signal from the received light. One possible example of such embodiments is given when the transmitter and the light sensing element are housed in a separate enclosure and it is difficult to reliably synchronize both. Another unsynchronized embodiment is given when one transmitter is used with multiple light receivers, each with its own processing unit, and synchronization is difficult.

FIG. 3 illustrates one typical installation of the sensor, where:

Components 101 through 114 are the same as those described for FIG. 1.

201 is the excitation light produced by emitter 101.

202 is the light reflected by the monitored surface and environment light for which the invention aims to minimize the detection in the sensing element 111. It includes components with wavelengths equal to or shorter than the cutoff wavelength of optical filter 112 if it is a long-pass filter or the first (lower) cutoff wavelength if 112 is a band-pass filter. At the optical filter 112, most of the light 202 is reflected away. However, a small amount of light 202 passes through 112 to reach sensing element 111 due to the filtering efficiency of 112 being almost always below 100%.

203 is fluorescence emitted by the materials to be detected, and environment light components with wavelengths longer than the cutoff wavelength of optical filter 112, and shorter than the second cutoff wavelength if 112 is a band-pass filter. At optical filter 112, most of light 203 passes through to reach the sensing element 111.

211 is the surface to be monitored. It can be a solid surface such as a floor or ground, or a liquid surface such as surface of a lake, sea surface or surface of water in a sump. It does not necessarily need to be horizontal but can be inclined or tilted at any angle.

212 is the hydrocarbon or other material to be detected, if present.

FIG. 4 illustrates the positioning of sensor 100 relative to the surface. Sensor 100 can be installed at different heights above the surface. For embodiments adapted to many indoor environments, such as generator rooms, industrial sites, inside marine vessels, or in rooms housing oil-based furnaces, the installation height (H) may be 3-10 feet (approximately 1-3 meters), or higher for larger rooms. For embodiments customized for aviation, the installation height will experience wider variations, from tens of meters for hangars, aviation fuel depots, runways, or landing pads; to heights from 1-20 ft (30 cm-6 meters) for embodiments installed on aircraft, ground vehicles or surface roaming devices. Installation heights will typically be much higher for installation on an offshore facility to stay above the reach of waves in severe weather. For miniaturized embodiments (compact printed circuit boards, lab-on-chip, or optoelectronic ASIC), the installation height can be from 30 cm to a few millimeters. The sensor can face vertically at the surface, which is usually the best direction for generating the largest signal, or aim at the surface with the optical centerline off perpendicular (angle θ) to 80 degrees in most embodiments, and very close to 90 degrees in certain embodiments.

Sensor 100 can be attached to a scanning mechanism which can vary the off-perpendicular angle θ and the azimuth angle of the sensor so that a larger area of the surface can be scanned. The sensor height H can also be adjusted during operations to increase the scanning coverage.

Regardless of mounting relative to the surface, one preferred sequence of monitoring operations is as follows:

1. While keeping emitter 101 off, measure light intensity ($L_{off,1}$) using sensing element 111,
2. Turn on emitter 101, measure light intensity ($L_{on}$),
3. Find the difference $LD=L_{on}-L_{off,1}$
4. Turn off emitter 101, measure light intensity ($L_{off,2}$),
5. Compare $L_{off,1}$ and $L_{off,2}$. Accept the data point if they are close to each other, that is, when $\Delta L_{off}$ (the absolute difference between $L_{off,1}$ and $L_{off,2}$) is small enough, otherwise reject the data point. The acceptance can be determined with several methods including combinations of multiple methods, for example,
   a. Method 1: The data point is accepted when the absolute value of the ratio of $\Delta L_{off}$ to LD ($|\Delta L_{off}/LD|$) is less than a threshold value C, which is typically 0.001 to 1 (but can also be outside this range) and is selected depending on the desired combination of sensitivity and accuracy of the detection for the particular application. Larger C values are used when higher sensitivity is needed (detecting the presence of oil quicker and having no or smaller number of missed alarms) and the accuracy of detection can be lower (the number of false alarms is not critical). Smaller C values are used when the accuracy of alarm (i.e., avoidance of false alarms) is more important than the sensitivity of detection.
   b. Method 2: The data point is accepted when $\Delta L_{off}$ for this data point is statistically within the range of $\Delta L_{off}$ measured when it was known that the surface is free of oil. With this method, a set of oil-free baseline measurements is needed before the detection operation. To measure the baseline, Steps 1-4 are repeated for a period of time when it is known that the surface is free of oil. The period of time is sufficiently long to cover the anticipated ambient light variations. For example, in a room with only artificial lighting and without access to sun or moon light, the period can be a few minutes during which time the artificial light is turned on and off a few times. In a location where direct or reflected sun or moon light can reach the surface to be monitored, the baseline may need to be a day or a few days, so that the variations of ambient light can be measured completely.

The average ($A_{baseline}$) and standard deviation ($\sigma_{baseline}$) of the baseline $\Delta L_{off}$ are calculated from the data. When evaluating the $\Delta L_{off}$ measured during the detection operation (this step), the data point is considered to be statistically within the range of $\Delta L_{off}$ measured when it was known that the surface is free of oil (the baseline) if the absolute difference between $\Delta L_{off}$ and the baseline average $a_{baseline}$ is less than a factor D multiplied by the baseline standard deviation $\sigma_{baseline}$:

$$|\Delta L_{off} - A_{baseline}| < D * \sigma_{baseline}$$

where D is typically 0.5 to 2 (but can also be outside this range) and is selected depending on the desired combination of detection sensitivity and accuracy of detection. Lower D values are used when high accuracy of detection is critical and is more important than high sensitivity of detection, and higher D value is used when it is critical to detect the presence of oil without missing.
6. If the data point is accepted, compare LD with the pre-determined threshold $LD_{min}$, which is the LD found when a sample representing the minimum amount of the material to be detected was placed in the monitored area. If LD is greater than $LD_{min}$, flag the point as potentially positive. The pre-determined threshold is selected through a calibration process, in which the minimum amount of oil required to be detected is placed on the surface to be monitored, and the LD is measured for a period of time, for example a few seconds or a few minutes. The average of LD measured during this time is the $LD_{min}$. Simulated surfaces can be used when it is not practical or not desirable to place oil directly on the surface to be monitored, for example when it is difficult to remove the oil after the calibration. In such cases, the simulated surfaces should be as close to the actual surface as possible, and a safety factor (typically 1.5-2) is applied to LD measured to reduce the average LD to a lower $LD_{min}$.

7. Repeat steps 1-6 for a period of time corresponding to the detection interval requirements for the application, for example 10 seconds, as explained below.
8. If the fraction of the potentially positive points in the total number of accepted data points during this period of time exceed a pre-selected value, which is typically 0.6 to 0.9, a signal is produced to indicate detection of the material.

Regarding Step 7, some scenarios may require an alarm within 30 seconds of fuel leakage. Therefore, in such situations, 10 seconds would be a reasonable detection interval. This interval leaves time for further actions from the detection to generation of the alarm, for example the time for a remote controller to receive the detection result via Modbus communication. If ambient light shifts, causing 10 seconds not to be achievable, i.e., when too few data points are available within 10 seconds to achieve statistical significance, the interval can be increased to 15 or 20 seconds. In applications where there is no specific requirements on detection timing, e.g., detection of a slowly evolving oil leak on a fresh water reservoir, an alarm might be issued within 5 minutes from the onset of oil, and therefore, a 2 minute interval could be used so that sufficient data points are collected to achieve statistical significance to reduce false alarm occurrences to near zero.

At Step 8, a fraction of potentially positive points of 0.6 would mean 60% of the valid points are positive, and 0.9 means 90% are positive. Thus, the likelihood of the true situation being positive is higher than negative.

Values chosen for Steps 7 and 8 depend upon requirements of a particular application: better alarm accuracy or faster response time. In applications where prompt mitigation measures are needed, such as fire prevention, a smaller value is used, so that the device produces alarms more quickly. For applications in which the accuracy of alarm is more important, for example in an oil field waste water pond, it is more important for every alarm to be a true alarm, as it may trigger the shutdown of a very large system operation, and there are follow-up means to clean up if the higher accuracy leads to some missed alarms associated with small leaks—for example, small amounts of oil can be skimmed off the water by mechanical means.

In some embodiments, sensing element 111 is a color CMOS, color CCD, or multispectral sensor, in which further alternatives or refinement of the procedure can be made by analyzing the light in several wavelength bands and comparing the signals in these bands with the characteristics of fluorescence spectra of various materials, thereby differentiating the type of material that is present. For example, crude oil of different origins, diesel, and other refined products have different fluorescence spectra and wavelengths at which the fluorescence peaks and the magnitude of the spectral shifts with thickness of the material, as illustrated in FIG. 5. The type and thickness of hydrocarbons can be determined by comparing the fluorescence spectrum detected with these known characteristics.

In yet other embodiments, sensing element 111 is a two-dimensional array of semiconductor light sensors, such as a typical digital camera sensor, in which the incoming signals from the area of the surface that is monitored is a two-dimensional matrix, that is, a digital image. Similar analyses can be conducted as above, but with the location-dependent matrix. The matrix can be analyzed to detect whether hydrocarbons are present, identify the location and boundary of the hydrocarbons, and calculate the amount of the hydrocarbons. Multiple methods can be used for this analysis, including:

Method 1: The difference of the images when the emitter is on and off can be determined by subtraction, and boundary detection algorithms can be applied.

Method 2: The images are subdivided into blocks, each block being small enough for detecting the minimum size of a hydrocarbon spot to be detected, and the light strength of each block is obtained from the average of all the pixels in the block. The light strength can be a combined strength of all colors (such as red, green, and blue), the strength of a single color, or a set of the strength of each wavelength interval. The difference of the light strength when the emitter is on and off is obtained, forming the signal at the block.

Method 3: Some embodiments of the invention use image processing algorithms such as feature extraction from the array of light intensity or difference field LD, aiming to identify connected shapes indicating potential fuel leaks. In yet other embodiments, these shapes are analyzed for dynamic growth behavior which may indicate continued leakage.

Method 4: Yet other embodiments rely on machine learning algorithms based on artificial neural networks (ANNs), for example convolutional neural network, deep learning neural networks, or recursive learning neural networks, to analyze the array of light intensity or difference field LD for the presence of hydrocarbon leaks. Supervised learning is employed for the initial training of the algorithm, where leaks of different sizes are generated through a real sensor or in a computer simulation. The algorithm is thus trained to recognize leaks above a severity which can be set through user-provided examples. In some of these embodiments, the algorithm continuously improves its performance by learning from successfully detected leaks or false alarms, as indicated by operator feedback. Some embodiments of ANNs may rely on the analysis of each subsequent image independently, whereas other embodiments may employ techniques from recurrent neural networks for time series analysis.

Method 2) is preferred when there is a stringent time constraint for detection, such as in fire prevention alarms, because it usually requires less intensive computing by the processing unit 122 than the other methods, therefore can respond faster. The more computationally intensive methods can also be used if the processing unit is capable of completing the analysis within the required response time, or through the help of an additional processing unit to accelerate the analysis.

In case Method 2) for two-dimensional images is employed, the time series of each block is analyzed as described in the following. When the condition for detection is met at a block, sensor 100 reports hydrocarbons present at the block. Further analysis can also be performed on the detection results, such as the total area of hydrocarbon, whether the total area exceeds the minimum for initiating an alarm, and whether the area is trending higher or lower, by analyzing the evolution of the number of positive blocks.

A typical operational procedure with this configuration is:

1. The baseline signals, which are the signals when the surface is known to be free of hydrocarbons, at each image block are established for a time period determined by the ambient light, and the scale of the area to be observed.

For typical indoor applications with sensors installed 3-10 feet from the area to be observed, said time period is typically 15-30 minutes. The time period is longer for larger areas and more intense ambient light such as in outdoor deployments, and shorter for miniaturized embodiments.

In some embodiments, the baseline may be established once and all sensors may be programmed with the same baseline, and in other embodiments, the baseline will be customized to a given deployment site. In some embodiments, a default baseline will be established, with an option for a site-specific override by the user.

For a period of time, the baseline signals at each block are obtained per the steps below:

a. While emitter 101 is off, take an image with sensing element 111.
   b. The image is divided into the pre-determined number of blocks. That is, the pixels of the images are grouped into multiple connected sub-areas, each containing multiple pixels, with a minimum of one pixel per sub-area. The same division will be kept throughout this operation procedure.
   c. The light magnitude $L_{off,1}$, of each block is calculated. When sensing element 111 is a color image sensor or spectral image sensor, the magnitudes of colors or spectra can be calculated as well. In general, for each of one or more ranges of wavelengths of interest, at least one first metric indicating the intensity of light detected and the spectral composition of the reflected light is extracted, such as the average or median signal among the pixels within a block, or the sum of all signals among the pixels within a block, or any other metric that increases with the amount of light detected,
   d. Turn on emitter 101. Repeat steps 1b and 1c to obtain the light magnitude $L_{on}$ of each block.
   e. Turn off emitter 101. Repeat steps 1b and 1c to obtain the light magnitude $L_{off,2}$ of each block.
   f. Compare $L_{off,1}$ and $L_{off,2}$. If the difference is sufficiently small, for example, if the change is less than 1%, accept the data point, otherwise reject the data point. Additional criteria, such as comparison of the difference with the expected minimum signal when hydrocarbons are present, can also be applied to fine tune the evaluation.
   g. If the data point is accepted, calculate the light magnitude increase for each block: $L_{on}-(L_{off,1}+L_{off,2})/2$. The light magnitude increase for each block is kept in a time series.
   h. At the end of the baseline collection, the time series of light magnitude for each block is analyzed for the average and standard deviations, which will be used in subsequent steps of the operational procedure.

2. The sensor is calibrated with hydrocarbon samples with the thickness and size meeting the detection threshold requirements. An example of a calibration target is a circular disk with at least one transparent glass windows with an aperture of 5 inches (127 mm) diameter and a chamber thickness of 0.078 inch (2 mm), which can be filled with any liquid hydrocarbon. The calibration steps are:

a. An empty sample container is placed at a location within the monitored surface area.
   b. The time series of light magnitude increase over ambient for each block is obtained in the same method as in Steps 1a-1f.
   c. After a suitable number of data points have been obtained, for example 100 points, the average light magnitude increase at each block is calculated from the time series.
   d. Fill the container with hydrocarbons or replace the container with another one with the same design but filled with hydrocarbons.
   e. Repeat Steps 2a-2c to obtain the set of signal data series and the average light magnitude increase at each block when hydrocarbons are present in some of the blocks.
   f. Block-wise subtract the two sets of averages to obtain the net increase at each block due to hydrocarbon. Find the maximum difference across the blocks and the corresponding location. This is the signal generated by the hydrocarbon sample.
   g. Repeat Steps 2a-2f with the container at other locations, or with other types and other thicknesses of hydrocarbons if it is desired to identify the type of hydrocarbon during monitoring.
   h. Analyze the signal at the locations and estimate the signal at each block if hydrocarbons were present.
   i. If multiple types of hydrocarbons are used in the calibration, record the fluorescence spectra of each type of hydrocarbon and each thickness.

3. Monitor the surface for detecting hydrocarbons using cycles of data collection and analysis:

a. Obtain signals following the same method as in Steps 1a-1g.
   b. Check each block of the image to determine whether hydrocarbons are present using a multiple-sigma approach or probability approach.

In the multiple-sigma approach, the block is flagged as potentially having hydrocarbons if the signal is sufficiently above baseline average (evaluated per the ratio of the difference over the standard deviation of baseline at the block) and is sufficiently close to the expected signal if hydrocarbons were to be present (also evaluated by multiples of the standard deviation of the baseline).

In the probability approach, the probability of hydrocarbon presence in the block can be calculated using normal probability distribution or other suitable probability distribution.
   c. Add the flag or probability result to the time series for each block
   d. Repeat Steps 3a-3c until the time has been reached to determine whether to raise an alarm for hydrocarbon presence. For example, if the device is required to detect hydrocarbon leakage within 30 seconds of occurring, the time may be every 20 seconds.

In general, through Steps 3b-3d, a time series of images representing hydrocarbon fluorescence signature are generated from the ordered array of data from the light sensing element 111, each item in the array corresponding to a location on the monitored surface and overall representing a map of hydrocarbon fluorescence signatures present on said surface.

e. If the multiple-sigma approach is used (following the selection in Step 3b), count the number of flags at each block and set the status of the block to Hydrocarbon in Block if the fraction of cycles with flags in the total cycles is over a threshold, for example 0.6-0.9, similar to that described earlier for the configurations with the light sensing element 111's reading as a single value. Otherwise, the status is set to No Hydrocarbon in Block.

If the probability approach is used (following the selection in Step 3b), the probabilities of hydrocarbons present at each block are kept in time series, and the cumulative probability of hydrocarbons present at the block are calculated; the status of the block is set to Hydrocarbon in Block if the cumulative probability exceeds a threshold probability, which is pre-determined depending on the acceptable false alarm rate and missed alarm rate. Otherwise, the status is set to No Hydrocarbon in Block.

If the total number of blocks with Hydrocarbon in Block status exceeds the minimum for an alarm, which has been pre-calculated with specified minimum amounts of hydrocarbons, an alarm for hydrocarbon presence is raised.

Other analysis procedures can also be applied. In general, the times series of Step 3d is analyzed to result in a second time series of quantitative metrics measuring apparent leaks in one or more parts of said images, and indicators of hydrocarbons leaking on said surface are generated based on the analysis.

f. If hydrocarbons are detected, and it is desired to determine the amount and outline of the hydrocarbon leak, the volume of hydrocarbons in each block is calculated using the signal for the block and the thickness-signal relationship obtained from prior calibration. The block-wise volumes are summed to obtain the total hydrocarbon volume. The block-wise volumes are tabulated for reporting, and for use in creating a scene image coded (highlighted with color codes, text coded added, or other suitable methods) with such volume data.

g. If hydrocarbons are detected, and if there are multiple sources of hydrocarbons that can potentially leak to the area, and it is desired to identify the material type, the fluorescence spectra from the blocks identified as having hydrocarbons are compared with the calibrated spectra to determine the best match, leading to identification of the hydrocarbon type. The type of materials detected and the locations (blocks) are tabulated for reporting, and for use in creating a scene image coded (highlighted with color codes, text coded added, or other suitable method) with such volume and chemical data.

h. Repeat Steps 3a-3g for the next operation cycle.

The alarm raised in Step 3e may result in at least one of the following: a user is alerted through visual- or audio-indication, the alarm is logged in a database, a switch is actuated through a control system, wherein said switch deactivates equipment that presents a potentially hazardous condition when operating in the presence of a hydrocarbon leak, another switch is actuated through a control system, wherein said another switch activates equipment that mitigates potentially hazardous conditions associated with a hydrocarbon leak.

FIG. 6 shows an example image collected and the monitoring results when sensing element 111 is an image sensor. The image has been divided into subgroups (blocks) for analysis. FIG. 6(*a*) shows the image collected and divided into blocks when emitter 101 is off. The plate, visible as a round object in the center-top area of the image in FIG. 6, contains a certain amount of hydrocarbons. FIG. 6(*b*) shows the image of the same area and also divided into blocks, with the difference compared to FIG. 6(*a*) that emitter 101 is on and the blocks determined to have hydrocarbons present are highlighted. The floor slopes up from the lower left of the image to the upper right of the image, resulting in an uneven spread of the hydrocarbons. The un-shaded blocks within the plate also have hydrocarbons, but the thickness is smaller than needed for generating fluorescence above the pre-specified threshold, and is consequently not identified by the sensor as having hydrocarbons.

In general, each image block contains at least one pixel of the imaging sensor, and typically much larger number of pixels are in each block. The number of blocks is chosen so that the dimension of each block is small enough to define the minimum size of a hydrocarbon leakage spot to be detected.

FIG. 7 is an illustration of the time series. FIG. 7(*a*) shows the flags for potential hydrocarbon presence in a certain block. FIG. 7(*b*) shows the probability for hydrocarbon presence in the same block. Step 3e described above uses data such as these to determine whether hydrocarbons are indeed present in the block. In this example, hydrocarbons are physically present in the block after Cycle 1050. Analysis of these data would trigger an alarm a few cycles after Cycle 1050, and no alarm until then.

Prior to Cycle 1050, there are no hydrocarbons present, so the signal is mostly very low, leading to no flag and low probability values. The signal in some cycles may be high due to interference of ambient light variation, vibrations, or other factors, so the analysis set flag for potential hydrocarbon presence and the probability is much higher than in cycles without interference. However, an alarm would not be raised for these cycles when the time series is analyzed due to either the total number of flags being lower than a threshold for the number of flags, or the cumulative probability being below a probability threshold. After Cycle 1050, the signal strength is generally high enough to cause the flag of potential hydrocarbon presence to be set, and the probability value is high. The signal is low in some cycles due to similar factors as those causing an interference-triggered "high" signal prior to Cycle 1050, leading to no flags set and the probability being also lower in these cycles than in adjacent cycles. However, time series analysis would still determine hydrocarbons to be present in these cycles, since there are enough cycles in the series having flags or high probability.

FIG. 8 illustrates a hydrocarbon sample container that can be used during calibration of sensor 100 or verification of the detection performance. The container fully seals the hydrocarbons to prevent accidental spillage during calibration. FIG. 8(*a*) is an isometric view of the container. FIG. 8(*b*) is an exploded view. FIG. 8(*c*) is a cross-sectional view. In the figure:

301 is a transparent pane with a non-fluorescent material. A preferred material is tempered optical glass with greater than 90% transmittance of light. High transmittance helps for the characteristics of the monitored surface to be well represented in the signal that the sensor receives. Another preferred material is acrylic.

302 is an elastomer seal in the form of gasket or O-ring.

303 is a ring of metal or plastic that has low or no fluorescence. The thickness of the ring is the same as the benchmark thickness to calibrate with or verify for, for example 0.078 inch (2 mm). Preferred materials include aluminum and nylon.

304 is an elastomer seal similar to 302.

305 are fasteners to attach the cover pane 301 to the ring 303. The number of fasteners to use depends on the cross dimension of the container, increasing in number for larger cross section dimensions.

306 is a pane of either transparent or opaque low-fluorescence material.

307 are fasteners similar as 305, for attaching the bottom pane 306 to the ring 303.

308 is the hydrocarbon sample to calibrate with. The hydrocarbons fill to the top of ring 303.

A variation of the container design is that 303, 304, 306 and 307 are replaced by a single part with a single material, forming a dish. The dish may include filling, vent and draining ports with suitable seals. The sample container in this variation consists of 301, 302, 305, and the dish. Another variation is for the transparent pane to be easily removable during calibration to avoid its absorption effects, such as through using latches or screws with wingnuts instead of the fasteners.

Typically, two containers are used. The two are identical except for one with hydrocarbons 308, and one without. The two are placed at the same location on the monitored surface, one replacing the other after data collection has been completed with it. During calibration, the signal with the empty container is used to adjust the signal with the filled container, so that the net effect of the hydrocarbons over the surface can be obtained.

Another use of the sample containers is for testing the leakage sensor, which is oftentimes required in regular intervals, such as once or twice a year, or once a month. Compared to other sensor technologies, which require lengthy procedures of introducing simulated leaks, followed by oftentimes unreliable sensor resets, the present invention thus provides a means to test the sensor which can be as short as a few minutes. The resulting reduction in technician-hours, along with the avoidance of any hazardous waste introduced, results in a considerable reduction in the cost of ownership. If the sample piece is used for such testing or verification, a new baseline is first obtained with the empty container placed, followed by monitoring after the container with hydrocarbon replacing the empty container.

In case Method 4 is employed for the analysis of the two-dimensional images and an artificial neural network is implemented for the detection of hydrocarbons, the artificial neural network (ANN) is trained to perform a classification task of two-dimensional images or a time series of two-dimensional images, or data attributes extracted from two-dimensional images. The most elementary classification are "negatives", i.e., the absence of a leak, and "positives", i.e., the presence of a leak. Other classifications may include growing or shrinking/evaporating leaks, or leaks caused by different types of hydrocarbons. Training the ANN comprises categorizing data samples into a priori known classifications.

"Negatives" are images, or data extracted from time series of images, associated with baseline situations (without hydrocarbons present, but with potential fluctuations in ambient light), or situations with amounts of hydrocarbons too small to warrant raising an alarm, or combinations of the latter two. In some embodiments, these "Negatives" may be associated with different classes that affect the operational state of the sensor. One such further sub-classification of "Negatives" is the following:

- "Inactive Negatives" may include situations with too much activity, such as maintenance, in the field of vision of the imaging sensor to ensure reliable operation of the algorithm, which may result in changing the operational state of the sensor to "Inactive". This is justified by operators being present, who would notice a hydrocarbon leak anyway, and may be accompanied by an "inactive" signal sent to a control center.
- "Active Negatives" are situations in which the activity or ambient light fluctuations in the field of vision are low enough to permit reliable hydrocarbon detection.

"Positives" are generally images of hydrocarbons leak which would warrant an alarm according to the standards present in the application site. Training image data may be acquired of containers such as shown in FIG. 8, of combinations of multiple containers as shown in FIG. 8, of flexible containers such as made of transparent rubber materials functionally similar to the container shown in FIG. 8, of real hydrocarbon leaks, or of targets modeled in computer simulations. Calibration targets with various shapes and sizes, containing hydrocarbon of various thickness and type, can be used to create the training data. In some embodiments, further positives subclassifications are presented in the following non-exhaustive list:

Types of hydrocarbons leaking (at least one class per type).

- Degree of hazard, such as growth rate of a leak (different classes according to hazard ratings).
- Growing versus shrinking or evaporating leaks.
- In conjunction with the overall image acquired in the scene, a classification of the source of the hydrocarbon leak (i.e., which part of a machinery).

The training data set is used by backpropagation, producing coefficients of the artificial neural network implemented, and the coefficients are saved. The saved coefficients of the artificial neural network are utilized to continuously monitor a surface by conducting, at regular or irregular time intervals, forward-propagation with the coefficients on the images acquired to classify the acquired data sets to evaluate the presence of hydrocarbon leaks on the surface.

The training data set can be improved as monitoring progresses, by evaluating with other means whether alarms are false or leakages are missed, and including the data for these scenarios in the training data set:

- Correct and false alarms: The indications of hydrocarbon leaks from the monitored surface are evaluated, wherein each correct positive score is classified as real hydrocarbon leak detected, and a false positive score is classified as leak indication which was not caused by a real hydrocarbon leak, wherein signals from the imaging sensor measured during indications of hydrocarbon leaks are stored in a data repository along with the correct positive score or false positive score, wherein said data repository is employed to generate an improved training data set from the original data set based on calibration targets, such as through updated backpropagation, followed by the production of improved artificial neural network coefficients, with the aim of reducing the number of false positives.
- Missed detections: The signals from measurements of the imaging sensor monitoring the surface are stored in a data buffer for a buffer period, wherein the monitored surface is tested for a hydrocarbon leak through another means, such as another sensor or visual verification by an operator, at least once during said buffer period, wherein a false negative score is assigned to the buffer period if a real hydrocarbon leak was not successfully indicated, wherein the data buffer and false negative score is stored in another data repository, wherein said another data repository is employed to generate an improved training data set, followed by updated back-propagation to produce improved artificial neural network coefficients, with the aim of improving the reliability of alarm indication.

FIG. 9 shows one example implementation of artificial neural network:

The circles represent the neurons of the network. 401, 402, 403 and 404 are groups of neurons in the input layer, 410 is an inner layer, and 420 is the output layer. There may be multiple inner layers 410.

The input layer takes input such as:

- Data from the latest measurement cycle, such as the signal due to the excitation light in the form of the total signal of all color components, any single color, or the full spectra.
- Block-wise results on flags or probabilities for hydrocarbon presence from earlier measurement cycles. In that case, the number of nodes are the number of blocks times the number of cycles in the observation interval.
- Block-wise baseline data.
- Other input data, such as the false alarm rate at blocks where such information is available.

The calibration data are not part of the input, since they have been used as training sets to develop coefficients of the network.

Each neuron in 401, 402, 403, and 404 produces one category of intermediate evaluation for an image block, such as whether the data for the given block from this cycle is valid for use, probabilities of hydrocarbon presence from this cycle's data and from historical data, weighting factors on the probabilities for estimating combined probability, likely type of hydrocarbon, etc.

Neurons in 410 uses the above responses from the input layer to produce estimation on whether hydrocarbons are present in each block, the amounts of hydrocarbons in each applicable block, and the types of hydrocarbons present.

Neurons in 420 produces outputs which may include one or more data from among the total amount of hydrocarbons present, whether to raise an alarm, a map of hydrocarbon locations, the type(s) of hydrocarbon present, or any other measurable quantity influenced by the hydrocarbons' fluorescence.

Depending on the needs of each particular application, the sensor hardware can take different forms from those described in FIGS. 1, 2 and 3. Possible configurations include:

- Light transmitter and light receiver are in two separate enclosures
- Multiple light receivers are used with one light transmitter
- The sensor, or a subsystem of the sensor, is mounted on a surface roaming robot that has the capability of autonomously and systematically cover the full area to be monitored, and feeding the in-situ location coordinates to the sensor,
- The light receiver, data processing and communication are built in the form of an Application-Specific Integrated Circuit.
- The light transmitter, light receiver, data processing and communication and other components for the sensor are all built in the form of an Application-Specific Integrated Circuit.

Figure 10:
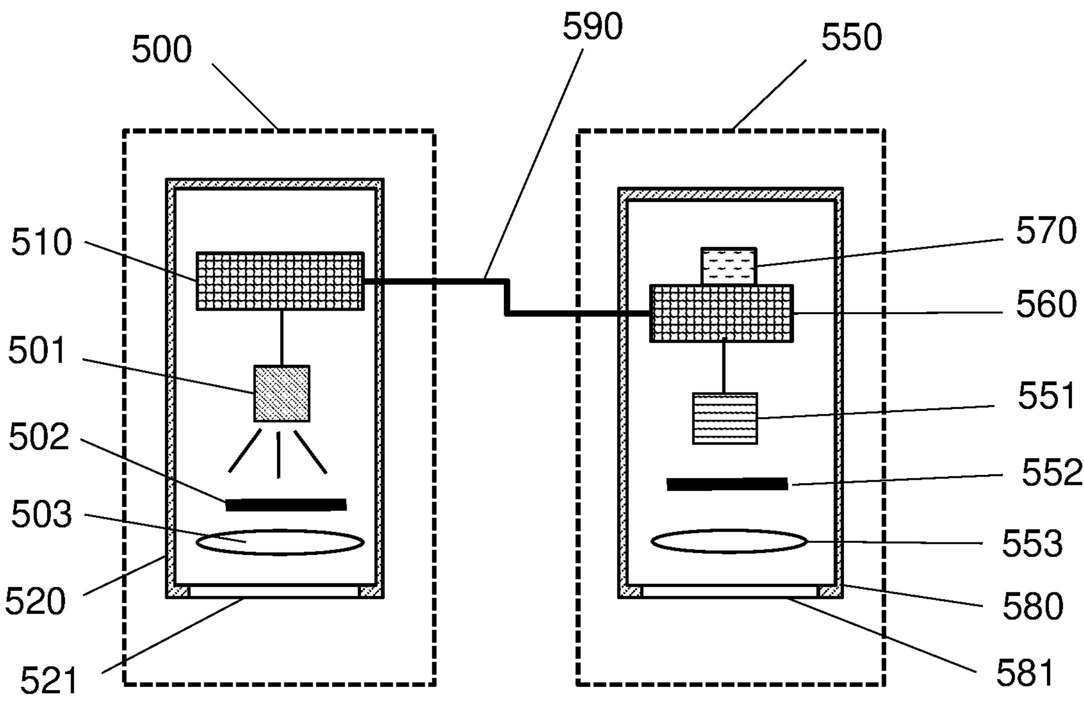

FIG. 10 illustrates the form wherein the light transmitter and light receiver are in separate enclosures:

500 is the light transmitter subsystem. It is comprised of components 501 through 521.

550 is the light receiver subsystem. It is comprised of components 551 through 581.

501 is an emitter of ultra-violet or visible light, similar to 101 in FIG. 1.

502 is an optional short-pass optical filter that blocks light component with wavelengths longer than a threshold value, similar to 102 in FIG. 1.

503 represents a lens or an assembly of lenses, to shape the light from 501 to cover the area of interest on the surface to be monitored, similar to 103 in FIG. 1.

510 is a power controller for the light transmitter capable of modifying the light intensity of the transmitter, for example by turning it on and off, or changing the light intensity in multiple steps. The modulation of light intensity can be from instructions by the Processing Unit in the light receiver subsystem 550 via wired or wireless communication, or can be autonomous, following a predetermined function of time, such as switching full power on and off at predetermined regular or irregular intervals.

Other components may also be present in the enclosure, which are not shown. These may include micro-controllers, communication modules and a power converter for converting external power supplies, other than from the light receiver subsystem 550, to the form needed for components in light transmitter subsystem 500.

520 is an enclosure for components 501 through 510, as well as other components for the transmitter subsystem.

521 is an optical aperture for the emitted light to pass through.

551 is the primary light sensing element of the sensor, similar to 111 in FIG. 1.

552 is a long-pass or band-pass optical filter, similar to 112 in FIG. 1.

553 is a lens or assembly of lenses, similar to 113 in FIG. 1.

560 is the electrical circuitry and digital processing unit. It includes:

- A power converter to convert power from an external source to provide power to the light transmitter 501,
- A signal conversion device which converts the light from light sensor 551 to electronic voltage readings. The signal conversion device may be an integral part of 551.
- An analog-to-digital converter which processes the electronic voltage readings and converts them into digital data representing light intensity. Where light sensor 551 is a color image sensor or multispectral sensor, the light intensity will be a set of values representing the strength of each color or spectral component.
- A Processing Unit capable of, and configured to, storing said digital data and running computer programs extracting the fluorescence signatures of hydrocarbons from said digital data.
- If needed for enhancing flexibility in implementing analysis algorithms, communication or other functions, a Second Processing Unit may be added.
- A power converter providing for said light sensor 551, said signal conversion device, said analog-to-digital converter, and said Processing Unit from an external power source,

570 is an optional component to connect with external networking devices using wireless communication protocol.

580 is a housing for components 551 through 570.

581 is an optical aperture for the reflected light and fluorescence emissions from the monitored surface to pass through.

590 is a group of wires that connect the transmitter subsystem with the receiver subsystem for power, communication, and control. Alternatively, the communication between the two subsystems can also be wireless, in which case suitable additional wireless communication modules are added to each subsystem, and a power converter module is added to the transmitter subsystem 500 to convert power from an external power source to the form required by the subsystem 500.

Figure 11:
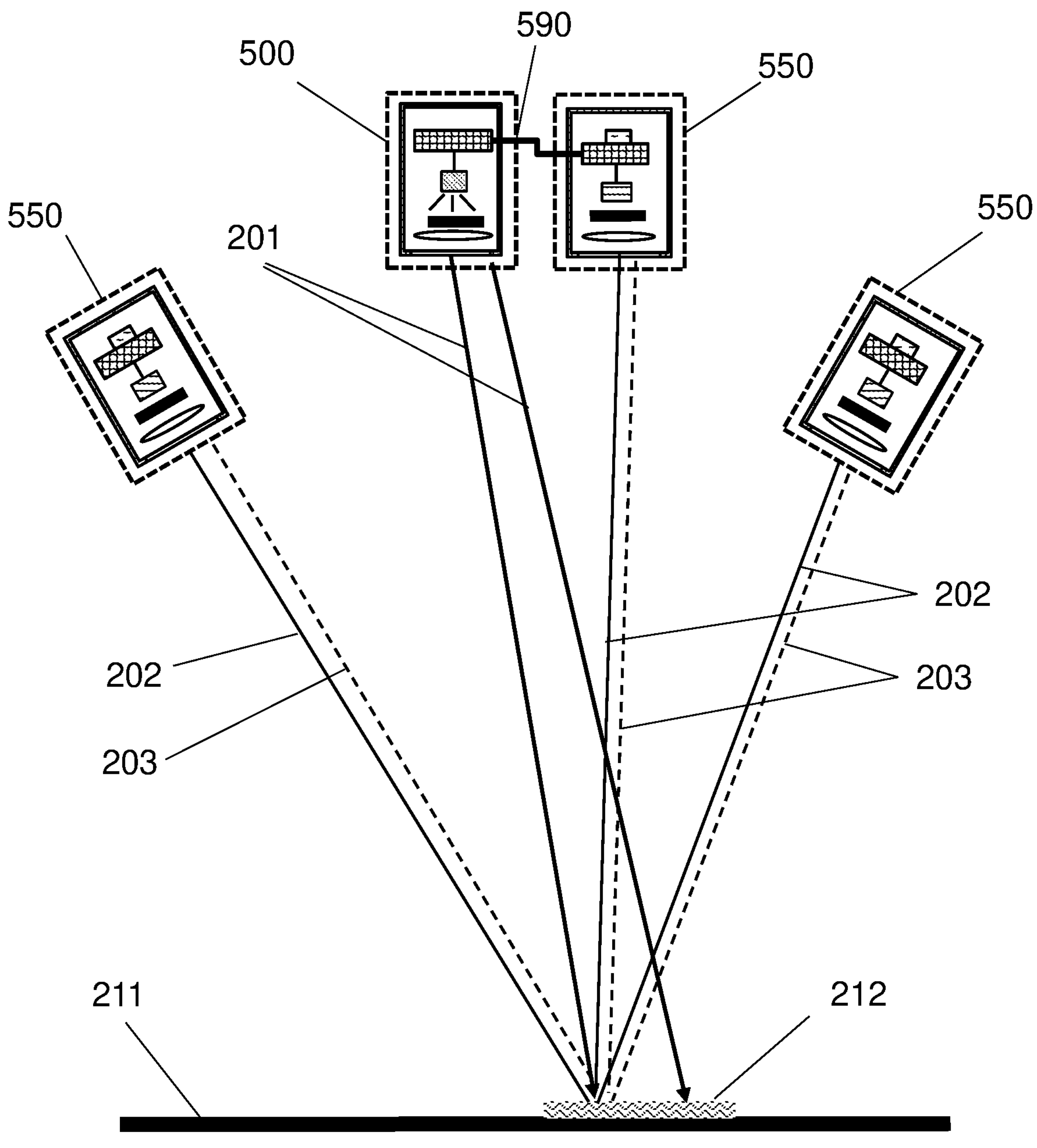

FIG. 11 illustrates the use of multiple light receiver subsystem with one light transmitter subsystem.

202 through 212 are as described for FIG. 2.

500, 550 and 590 are as described for FIG. 10.

In this form, only one receiver subsystem needs to provide power and light modulation signal to the transmitter subsystem. The transmitter subsystem may include a power converter, micro-controller or computer, communications, and other modules. The modulation of light intensity can be from instructions by the Processing Unit in the light receiver subsystem 550 via wired or wireless communication, or can be autonomous, following a predetermined function of time, such as switching full power on and off at predetermined regular or irregular intervals.

In some embodiments of the invention, the Processing Unit may be located in the transmitter subsystem instead of in the receiver subsystem, in particular if there are multiple receivers and only one transmitter, such as in FIG. 11.

Some or all components of the sensor (100) or one of the subsystems (500 and 550), can be integrated into one single miniaturized electronic component, such as an application-specific integrated circuit or lab-on-chip. There are multiple variations:

The light sensor (e.g., 111 from FIG. 1 or 551 from FIG. 10) in the light receiver subsystem (e.g., 550 from FIG. 10); some or all of the electrical circuitry and digital subsystems included (e.g., shown in 560 from FIG. 10), including the signal conversion device, the analog-to-digital converter, the Processing Unit; and optionally any power converters are integrated into the application-specific integrated circuit. The light transmitter subsystem is not miniaturized. Typically, this is done for applications in which high power excitation light is required, and it is technically or economically more advantageous to have the light transmitter and accessories to be of ordinary, non-miniaturized, size. For example, it may be technically easier and cost less to manage the heat generated by the light source when ordinary sized heat sinks are used. With the miniaturized light receiver subsystem, or part of the subsystem, the overall sensor size can be reduced if all components are in one single enclosure, or the light receiver subsystem's size can be much reduced, enabling deployment of the sensor or the light receiver subsystem in locations otherwise difficult to reach. In some embodiments, the lens or lens assembly (e.g., 553 in FIG. 10) are inside the one-single enclosure, whereas a lens assembly may comprise part of the enclosure itself in other embodiments.

Additionally, the light transmitter (e.g., 101 in FIG. 1 or 501 in FIG. 10); the power controller and power converter for the light transmitter (e.g., 510 in FIG. 10); and any one or more of the components shown inside the light transmitter housing (e.g., 520 in FIG. 10) can also be miniaturized and integrated into the same application-specific integrated circuit as the receiver assembly, or a second ASIC. This further reduces the dimensions of the components inside the sensor enclosure (e.g., 100 from FIG. 1 or 500 from FIG. 10) and makes the sensor smaller. In some embodiments, the lens or lens assembly (e.g., 503 in FIG. 10) are inside the enclosure, whereas a lens assembly may comprise part of the enclosure itself in other embodiments.

All sensor components can be fully integrated in one miniaturized enclosure or application-specific integrated circuit. The fully integrated system can be implemented as a semiconductor package containing the integrated circuit. Usually this will be for close-distance monitoring, suitable for applications such as installing below equipment or in ground vehicles and installing near locations on equipment susceptible to developing leakage, for example, low spots of piping for hydrocarbons that contains a certain amount of water.

The sensor (e.g., 100 in FIG. 1) or one of the subsystems (e.g., 500 and 550 in FIG. 10), whether in the form shown in FIGS. 1, 10 and 11, or in miniaturized form, can also be mounted on a wireless or wired device that roams the monitored surface and is capable of providing location coordinates to the Processing Unit of the sensor (e.g., 100 in FIG. 1 or the receiver subsystem 550 in FIG. 10). The location coordinates are used along with the light 956 intensity data in the analysis performed by the Processing Unit. Mounting all or part of the sensor on the roaming device has the benefits of increasing the signal strength, by locating the light transmitter close to the surface, locating the light sensor close to the surface, or both. Mounting the light transmitter on the surface roaming device reduces the spread of the excitation light, which is sometimes advantageous, for example, when it is desired to limit the exposure of locations not needing to be monitored by the excitation light.

The fully integrated system package can also be packages in a form factor designed to float on water, and with location tracking and long-range communication capabilities, to flow with river water and detect locations where hydrocarbons or other fluorescent materials are present.

VARIATIONS OF THE CONFIGURATIONS

The configuration can be varied for different applications without changing the principles of the invention.

What is claimed is:

1. A method for detecting hydrocarbons on a surface, comprising:

a. Irradiating a surface with a light source with a spectral band composition of incident wavelengths with a range of 100 nm-600 nm, b. Collecting fluorescence emissions and reflected light from said surface with a lens assembly with at least one convex lens and at least one optical filter, wherein said lens assembly is adjusted to create an image on an image plane located on the opposite side of said lens assembly relative to said surface, wherein said optical filter blocks transmission of all or most of said band of incident wavelengths, c. repeatedly measuring an intensity of light in at least one location on said image plane using at least one light sensing apparatus sensitive to visible wavelengths, d. determining the difference of said measured intensity of light from a baseline intensity for each measurement determining either, i) for each measurement if there is a high likelihood that a leak event occurred, wherein a high likelihood of said leak event is determined if the measured intensity exceeds a multiple-sigma threshold, a hydrocarbon area or volume indication threshold, or both, then updating a count of the number of occurrences of said leak event having said high likelihood during an observation interval, or ii) determining for each measurement a probability that a leak event has occurred, then determining a cumulative probability of a leak event having occurred during an observation interval which consists of one or more measurements described in steps a), b) and c), e. generating indicators for hydrocarbons leaking if a number of leak events during said observation interval exceeds a number threshold, or if said cumulative probability exceeds a threshold.

2. The method for detecting hydrocarbons on a surface of claim 1, further comprising, determining said baseline intensity by measuring said intensity of light a first number of times during a baseline measurement interval under conditions in which no leaks are present, wherein said baseline intensity is computed as a first quantitative metric representing the light intensity over said baseline measurement interval, including the average or median of said first number of intensity measurements, wherein said baseline measurement interval is longer than said observation interval.

3. The method for detecting hydrocarbons on a surface of claim 1, wherein the multiple-sigma threshold, a hydrocarbon area or volume indication threshold, or both, and spectral signatures of the hydrocarbon's fluorescence are determined by introducing hydrocarbon calibration targets on at least one location on said surface and repeatedly measuring said intensity of light a second number of times during a calibration interval, wherein a second quantitative metric representing the light intensity over said calibration interval, including the average or median of said second number of intensity measurements, is determined, wherein said hydrocarbon area or volume indication threshold is a function of the amount of said second quantitative metric over said baseline intensity.

4. The method for detecting hydrocarbons on a surface of claim 3, wherein said at least one calibration target represents a smallest leak the implementation of the method is aimed to detect according to at least one of the following criteria:

a) smallest lateral dimension to be detected, including such as represented by the smallest diameter of a circular calibration target, b) smallest thickness to be detected, or c) type of hydrocarbon representing the smallest fluorescence signal for a given lateral dimension and thickness.

5. The method for detecting hydrocarbons on a surface of claim 4, wherein at least one calibration target is a circular disk said circular disk having at least one transparent glass window which is filled with any liquid hydrocarbon.

6. The method for detecting hydrocarbons on a surface of claim 1, wherein said multiple-sigma threshold is determined by multiplying sigma, wherein sigma is a standard deviation of the baseline intensities, and a numerical factor, in which said numerical factor is a pre-selected fixed value or a value progressively-adjusted for optimizing a balance between high detection sensitivity and low false alarm rate.

7. The method for detecting hydrocarbons on a surface of claim 1, wherein the probability of said leak event occurring at a measurement described in steps a), b) and c) of claim 1 is calculated from an amount that the measured light intensity is above the baseline intensity to a standard deviation of the baseline, with a normal or other suitable probability density distribution.

8. The method for detecting hydrocarbons on a surface of claim 1, wherein said observation interval is shorter than response times mandated by fire protection standards.

9. The method for detecting hydrocarbons on a surface of claim 1, wherein said at least one light sensing apparatus is a semiconductor sensor array containing pixels, wherein said sensor array is grouped into multiple connected sub-areas, each sub-area containing multiple pixels with a minimum of one pixel per sub-area, wherein for each of said sub-areas, a third quantitative metric representing a light intensity over a calibration interval is determined.

10. The method for detecting hydrocarbons on a surface of claim 1, wherein said number of leak events during said observation interval is determined for each sub-area based on said third quantitative metric for each respective sub-area, wherein indicators for hydrocarbon leaking are generated if said number of leak events during said observation interval exceeds a number threshold for a minimum number of sub-areas.

11. The method for detecting hydrocarbons on a surface of claim 1, further comprising, wherein said cumulative probability of said leak event occurring during said observation interval is determined for each sub-area based on said third quantitative metric for each respective subarea, and wherein indicators for hydrocarbon leaking are generated if said cumulative probability during said observation interval exceeds the threshold for a minimum number of sub-areas.

12. The method for detecting hydrocarbons on a surface of claim 1, further comprising, determining a type of hydrocarbon leaked by best matching between the spectral composition of the detected light and the spectral signatures of the fluorescence from the hydrocarbons, if there are multiple sources of hydrocarbon that may have leaked to the area and a leak has been determined.

* * * * *